(12) United States Patent
Wagner

(10) Patent No.: US 11,759,429 B2
(45) Date of Patent: Sep. 19, 2023

(54) VACCINE DELIVERY SYSTEMS USING YEAST CELL WALL PARTICLES

(71) Applicant: ORBIS HEALTH SOLUTIONS, LLC, Greenville, SC (US)

(72) Inventor: Thomas E. Wagner, Greenville, SC (US)

(73) Assignee: Orbis Health Solutions, LLC, Greenville, SC (US)

( * ) Notice: Subject to any disclaimer, the term of this patent is extended or adjusted under 35 U.S.C. 154(b) by 0 days.

(21) Appl. No.: 17/532,656

(22) Filed: Nov. 22, 2021

(65) Prior Publication Data

US 2022/0151943 A1    May 19, 2022

Related U.S. Application Data

(62) Division of application No. 16/893,986, filed on Jun. 5, 2020, now Pat. No. 11,179,343, which is a division of application No. 16/227,468, filed on Dec. 20, 2018, now Pat. No. 10,675,249, which is a division of application No. 15/123,479, filed as application No. PCT/US2015/018728 on Mar. 4, 2015.

(60) Provisional application No. 61/948,503, filed on Mar. 5, 2014, provisional application No. 62/060,124, filed on Oct. 6, 2014.

(51) Int. Cl.
| | |
|---|---|
| *A61K 39/00* | (2006.01) |
| *A61K 9/50* | (2006.01) |
| *A61K 31/70* | (2006.01) |
| *A61K 31/7088* | (2006.01) |
| *C12N 1/16* | (2006.01) |
| *A61K 9/19* | (2006.01) |
| *A61K 39/39* | (2006.01) |

(52) U.S. Cl.
CPC .............. *A61K 9/5068* (2013.01); *A61K 9/19* (2013.01); *A61K 31/70* (2013.01); *A61K 31/7088* (2013.01); *A61K 39/0011* (2013.01); *A61K 39/39* (2013.01); *C12N 1/16* (2013.01); *A61K 2039/5154* (2013.01); *A61K 2039/55561* (2013.01); *A61K 2039/55572* (2013.01); *A61K 2039/55588* (2013.01); *A61K 2039/60* (2013.01)

(58) Field of Classification Search
None
See application file for complete search history.

(56) References Cited

U.S. PATENT DOCUMENTS

| | | |
|---|---|---|
| 4,454,110 A | 6/1984 | Caslavsky et al. |
| 4,563,351 A | 1/1986 | Casvalsky et al. |
| 5,032,401 A | 7/1991 | Jamas et al. |
| 5,340,740 A | 8/1994 | Petitte et al. |
| 5,607,677 A | 3/1997 | Jamas et al. |
| 7,740,861 B2 | 6/2010 | Ostroff |
| 8,926,994 B2 | 1/2015 | Serda et al. |
| 10,675,249 B2 | 6/2020 | Wagner |
| 2001/0006623 A1 | 7/2001 | Warford, III et al. |
| 2005/0059151 A1 | 3/2005 | Bosch |
| 2005/0158856 A1 | 7/2005 | Edelson et al. |
| 2005/0281781 A1 | 12/2005 | Ostroff |
| 2006/0083718 A1 | 4/2006 | Ginns et al. |
| 2006/0104986 A1 | 5/2006 | Duke et al. |
| 2006/0140983 A1 | 6/2006 | Palucka et al. |
| 2008/0167268 A1 | 7/2008 | Yan |
| 2008/0254537 A1 | 10/2008 | Boynton et al. |
| 2009/0209624 A1 | 8/2009 | Ginns et al. |
| 2009/0226528 A1 | 9/2009 | Czech et al. |
| 2010/0040656 A1 | 2/2010 | Franklin et al. |
| 2010/0111985 A1 | 5/2010 | Schwamberger et al. |
| 2010/0136102 A1 | 6/2010 | Franklin et al. |
| 2010/0166751 A1 | 7/2010 | Ostroff et al. |
| 2010/0221357 A1 | 9/2010 | Ostroff |
| 2012/0070376 A1 | 3/2012 | Ostroff et al. |
| 2013/0052220 A1 | 2/2013 | Duke et al. |
| 2014/0065173 A1 | 3/2014 | Wagner |
| 2014/0065190 A1 | 3/2014 | Wagner |
| 2014/0161912 A1 | 6/2014 | Wagner |
| 2014/0363872 A1 | 12/2014 | Jaroch et al. |

FOREIGN PATENT DOCUMENTS

| | | |
|---|---|---|
| JP | 408143447 A | 6/1996 |
| WO | WO 99/30629 A1 | 6/1999 |
| WO | WO 02/39951 A2 | 5/2002 |
| WO | WO-2004/014320 A2 | 2/2004 |
| WO | WO 2004/021994 A2 | 3/2004 |
| WO | WO 2006/044923 A2 | 4/2006 |
| WO | WO 2007/092792 A2 | 8/2007 |
| WO | WO 2009/102465 A2 | 8/2009 |
| WO | WO 2011/053331 A1 | 5/2011 |
| WO | WO 2011/131472 A1 | 10/2011 |
| WO | WO 2012/024229 A1 | 2/2012 |
| WO | WO 2012/082450 A2 | 6/2012 |
| WO | WO 2014/040089 A1 | 3/2014 |
| WO | WO 2015/030613 A1 | 3/2015 |

OTHER PUBLICATIONS

U.S. Appl. No. 15/252,999, filed Aug. 31, 2016, Wagner.
U.S. Appl. No. 15/751,640, filed Aug. 10, 2016, Wagner.
Chiarella et al., Adjuvants in vaccines and for immunisation: current trends, Expert Opinion on Biological Therapy, 2007, 7(10): 1551-1562.
Cole et al., "Novel Strategies to Enhance Vaccine Immunity against Coccidioidomycosis," PLOS Pathogens, Dec. 2013, 9(12):e1003768, 1-4.
Colino et al., "Dendritic Cells Pulsed with Intact *Streptococcus pneumonia* Elicit both Protein- and Polysaccharide-specific Immunoglobulin Isotype Responses In Vivo through Distinct Mechanisms," J. Exp. Med., Jan. 7, 2002, 195(1):1-13.

(Continued)

*Primary Examiner* — Jennifer E Graser
(74) *Attorney, Agent, or Firm* — Foley & Lardner LLP

(57) ABSTRACT

The present invention generally relates to compositions and methods for delivering a vaccine. The compositions and methods disclosed herein are particularly useful in making prophylactic and therapeutic vaccines.

5 Claims, 9 Drawing Sheets

(56) References Cited

OTHER PUBLICATIONS

Day et al., Eds., "Cryopreservation and Freeze-Drying Protocols," Methods in Molecular Biology, Second Ed., 2007, p. 10, Table 4.
De Nobel et al., "Increased Cell Wall Porosity in *Saccharomyces cerevisiae* after Treatment with Dithiothreitol or EDTA," Journal of General Microbiology, 1989, 135:2077-2084.
Figueiredo et al., "Yeast cell wall particles: a promising lass of nature-inspired microcarriers for multimodal imaging," Chem. Commun., 2011, 47:10635-10637.
Foged et al., "Particle size and surface charge affect particle uptake by human dendritic cells in an in vitro model," International Journal of Pharmaceutics, 2005, 298:315-322.
Goforth et al., "Immune stimulatory antigen loaded particles combined with depletion of regulatory T-cells induce potent tumor specific immunity in a mouse model of melanoma," Cancer Immunol. Immunother., 2009, 58:517-530.
Hong et al., "Organic/inorganic double-layered shells for multiple cytoprotection of individual living cells," Chemical Science, 2015, 6:203-208.
Huang et al., "Characterization and Optimization of the Glucan Particle-Based Vaccine Platform," Clinical and Vaccine Immunology, Oct. 2013, 20(10):1585-1591.
Huang et al., "Robust Stimulation of Humoral and Cellular Immune Responses following Vaccination with Antigen-Loaded β-Glucan Particles," MBio, Jul./Aug. 2010, 1(3):e00164-10, 1-7.
Jain et al., "Targeted drug delivery to macrophages," Expert Opinion on Drug Delivery, 2013, 10(3):353-367.
Kotera et al., "Comparative Analysis of Necrotic and Apoptotic Tumor Cells as a Source of Antigen(s) in Dendritic Cell-based Immunization," Cancer Research, Nov. 15, 2001, 61:8105-8109.
Mahony et al., "Mesoporous Silica Nanoparticles Act as a Self-Adjuvant for Ovalbumin Model Antigen in Mice," Small, 2013, 9(18):3138-3146.
Mueller et al., "Coencapsulation of tumor lysate and CpG-ODN in PLGA-microspheres enables successful immunotherapy of prostate carcinoma in TRAMP mice," Journal of Controlled Release, 2012, 162:159-166.
PubChem, 2015, Compound Summary for CID 6517 "Tetraethyl orthosilicate," 49 pages.
Sauter et al., "Consequences of Cell Death: Exposure to Necrotic Tumor Cells, but Not Primary Tissue Cells or Apoptotic Cells, Induces the Maturation of Immunostimulatory Dendritic Cells," J. Exp. Med., Feb. 7, 2000, 191(3):423-433.
Soto et al., "Characterization of Multilayered Nanoparticles Encapsulated in Yeast Cell Wall Particles for DNA Delivery," Bioconjugate Chem., 2008, 19:840-848.
Soto et al., "Glucan Particles for Macrophage Targeted Delivery of Nanoparticles," Journal of Drug Delivery, vol. 2012 (2011), Article ID 143524, 13 pages.
Strome et al., "Strategies for Antigen Loading of Dendritic Cells to Enhance the Antitumor Immune Response," Cancer Research, Mar. 15, 2002, 62:1884-1889.
Xia et al., "Porous Silicon Microparticle Potentiates Anti-Tumor Immunity by Enhancing Cross-Presentation and Inducing Type I Interferon Response," Cell Reports, 2015, 11:957-966.
Schnurr et al., "Tumor Cell Lysate-pulsed Human Dendritic Cells Induce a T-Cell Response against Pancreatic Carcinoma Cells: an in Vitro Model for the Assessment of Tumor Vaccines," Cancer Research, Sep. 1, 2001, 61:6445-6450.
Bauer et al., "Dendritic cell-based vaccination of patients with advanced pancreatic carcinoma: results of a pilot study," Cancer Immunol Immunother, 2011, 60:1097-1107.
Waeckerle-Men et al., "Encapsulation of proteins and peptides into biodegradable poly(D,L-lactide-co- glycolide) microspheres prolongs and enhances antigen presentation by human dendritic cells," Vaccine, 2006, vol. 24, pp. 1847-1857.
Waeckerle-Men et al., "Phenotype and functional analysis of human monocyte-derived dendritic cells loaded with biodegradable poly(lactide-co-glycolide) microspheres for immnunotherapy," Journal of Immunological Methods, 2004, vol. 287, pp. 109-124.

VACCINE DELIVERY SYSTEMS USING YEAST CELL WALL PARTICLES

CROSS-REFERENCE TO RELATED APPLICATIONS

This application is a Divisional of U.S. application Ser. No. 17/532,656, filed Nov. 22, 2021, which is a Divisional of U.S. application Ser. No. 16/227,468, filed Dec. 20, 2018, which is a Divisional of U.S. application Ser. No. 15/123,479, which is the U.S. National Stage application of PCT/US2015/018728, filed Mar. 4, 2015, which claims priority from U.S. Provisional Application Nos. 61/948,504, filed Mar. 5, 2014, and 62/060,124, filed Oct. 6, 2014.

FIELD OF THE INVENTION

The present invention generally relates to compositions comprising yeast cell wall particles and methods for delivering a vaccine. The compositions and methods disclosed herein are particularly useful in making prophylactic and therapeutic vaccines.

BACKGROUND OF THE INVENTION

A vaccine is a biological material or preparation that induces an immunologically mediated resistance to certain diseases upon administration to a subject. Vaccines have been widely used for the past 200 years in fighting against infectious diseases and non-infectious diseases.

Vaccines comprise an immunogen, which is an antigen that is capable of inducing humoral and/or cell-mediated immune response of the subject. Antigen presenting cells, including macrophages and other cells of the mononuclear phagocyte system actively phagocytose antigen particles and play a central role in the immune response. Macrophages are cells within the tissues that are derived from monocytes. These monocytes/macrophages phagocytose microbes are then digested to smaller antigenic portions in the lysosome/phagosome. The resultant antigens are cycled back to the surface for presentation to the humoral and cellular arms of the immune system. Accordingly, monocytes/macrophages are of particular interest because they play an important role in both nonspecific and specific defenses in the host against pathogens.

Dendritic cells are also antigen presenting cells that express MHC class I and class II molecules. In addition to the conventional dendritic cells, dermal dendritic cells are important members of the skin immune system. This is because dermal dendritic cells bear high amounts of MHC class II molecules and therefore can serve as very potent antigen presenting cells.

An ideal vaccine mimics the rapid uptake and transfer of pathogenic structures without actually establishing an infection and without causing suppression of the MHC class I pathway.

Recently, many studies have focused on targeted delivery of biological materials to a cell of monocytic origin to improve therapeutic effects of the biological materials. It was reported that many vehicles, including microspheres/microparticles, liposomes, nanoparticles, dendrimers, niosomes, and carbon nanotubes could be used for this purpose. It is desirable to achieve sustained delivery, extended duration of action, reduced dose and adverse side effects, and improved patient compliance with this new delivery approach. Jain et al., *Expert Opin. Drug Deliv.* 10(3): 353-367 (2013).

Yeast cell wall particles became one of the preferred delivery vehicles because of the hollow, porous microsphere structure formed by the glucan shell derived from a natural source, yeast. Soto et al., *Journal of Drug Delivery* 2012 (2011). Yeast cell wall particles were used in delivering various substances, such as nucleic acids, proteins, and imaging reporters. See, for example, Bioconjug. Chem. 19(4): 840-848 (2008); and Figueiredo et al., *Chemical Communications* 47: 10635-10637 (2011).

There remains a need in the art to improve immunization by efficiently delivering vaccines comprising exogenous proteins, epitopes, antigens, peptides, and/or nucleic acids for MHC presentation with only a very low amount of exogenous material. In addition, there is a need in the art to provide yeast cell wall particles for delivering biological materials to improve delivery efficiency, and to reduce the amount of biological materials to achieve the same or increased level of efficacy that targets cells of monocytic origin. The present invention satisfies this need.

SUMMARY OF THE INVENTION

In one aspect, the present invention relate to a composition for delivering a vaccine, comprising (i) a particle and (ii) an exogenous biological material such as a protein or a fragment thereof, nucleic acid, carbohydrate, tumor lysate, or a combination thereof, loaded within the particle. In specific embodiments, the vaccine comprises an antigen that induces an immune response upon administration to a subject. Preferably, the antigen or a fragment thereof is ultimately presented on a class I MHC molecule or a class II MHC molecule.

In some embodiments, the protein or fragment thereof, or nucleic acid is selected from the group consisting of a protein, a peptide, an epitope, an antigen, DNA, RNA, cDNA, and an immunogenic fragment or a subunit thereof. In other embodiments, the vaccine is a live vaccine, a killed vaccine, or an attenuated vaccine. In yet other embodiments, the vaccine is a recombinant vaccine.

In some embodiments, the particle is a digestable or biodegradable particle. Particles suitable for this invention are either synthetic or from a natural source, having a hollow inside or a porous structure. Exemplary particles include yeast cell wall particles.

In some embodiments, the loaded particle is incubated with an isolated dendritic cell for about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour, prior to administration. Preferably, the dendritic cell is an immature cell that has been isolated for no more than 8 days. In other embodiments, the loaded particle is administered without prior incubation with a dendritic cell population.

In some embodiments, the composition of the present invention further comprises one or more adjuvants, excipients, and/or preservatives. It is within the purview of one of ordinary skill in the art to select suitable adjuvants, excipients and/or preservatives for a particular vaccine.

In a preferred embodiment, a small amount of one or more immune response enhancing adjuvants is added to the composition. The addition of one or more adjuvants increases the immunogenic effects of the vaccine. Commonly used adjuvants include but are not limited to proteins, peptides, nucleic acids and carbohydrates. Exemplary adjuvants include but are not limited to monophosphoryl lipid A, CpG ologonucleotides (such as CpG DNA), Poly I:C, Poly ICLC, potent MEW II epitope peptides, beta glucan, and dendritic cell stimulating cytokines such as IL-12 and IFN-γ, as well as DC maturing cytokines such as IL-4 and GM-CSF. Suitable adjuvants are those molecules known to mature DC and interact with receptors on dendritic cells in order to activate dendritic cells and further stimulate a more robust generation of T cells, such as CD4+ and CD8+ T cells.

In one embodiment, the amount of one or more immune response enhancing adjuvants is at least about 10 ng, at least about 50 ng, at least about 100 ng, at least about 200 ng, at least about 300 ng, at least about 400 ng, at least about 500 ng, at least about 600 ng, at least about 700 ng, at least about 800 ng, at least about 900 ng, at least about 1 μg, at least about 5 μg, at least about 10 μg, at least about 15 μg, at least about 20 μg, at least about 25 μg, at least about 30 μg, at least about 35 μg, at least about 40 μg, at least about 45 μg, at least about 50 μg, at least about 60 μg, at least about 70 μg, at least about 80 μg, at least about 80 μg, at least about 90 μg, or at least about 100 μg. In one embodiment, the amount of adjuvant represents between 1-10% of the composition. The amount of adjuvant is sufficient to stimulate receptors, such as the toll-like receptor, on the dendritic cell.

In a related aspect, the present invention relates to a method for efficient delivery of a vaccine to a subject comprising directly administering to the dermis of the subject a composition comprising (i) a particle and (ii) an exogenous protein or a fragment thereof, nucleic acid, or a combination thereof, loaded within the particle, as disclosed above. The dermal dendritic cells phagocytose the loaded particle, thereby triggering the immune response to the vaccine.

In yet another related aspect, the present invention relates to a method for producing an incubated dendritic cell containing a biological material loaded particle comprising: (i) loading a biological material into the particle to produce the loaded particle; (ii) freeze-drying the biological material loaded particle; and (iii) incubating the biological material loaded particle with a dendritic cell, wherein the biological material comprises a protein or a fragment thereof, nucleic acid, or a combination thereof, and wherein incubating the loaded particle with the dendritic cell causes the dendritic cell to phagocytose the loaded particle.

In specific embodiments, the foregoing method further comprises (a) resuspending the biological material loaded particle in solution and (b) freeze-drying the resuspended solution before step (iii). The biological material comprises a protein or a fragment thereof, nucleic acid, or a combination thereof.

In specific embodiments, step (iii) comprises: (a) adding a biological material into a yeast cell wall particle, (b) incubating the yeast cell wall particle, (c) freeze-drying the yeast cell wall particle and (d) washing the yeast cell wall, wherein the biological material comprises a protein or a fragment thereof, nucleic acid, or a combination thereof, and wherein steps (b)-(c) are repeated at least once with a step of adding water into the yeast cell wall particle before step (b) is repeated.

In specific embodiments, step (iii) comprises: (a) contacting the vaccine loaded particle and the dendritic cell at a ratio from about 1:1 to about 100:1, including about 1:1, about 10:1, about 20:1, about 30:1, about 40:1, about 50:1, about 60:1, about 70:1, about 80:1, about 90:1, and about 100:1; (b) incubating the vaccine loaded particle with the dendritic cell for 1 to 2 hours and (c) collecting the dendritic cell and washing the cell.

Furthermore, the present invention relates to a method for preventing and treating infectious diseases and noninfectious diseases, comprising administering a composition comprising (i) a particle and (ii) an exogenous biological material loaded within the particle, wherein the biological material comprises a protein or a fragment thereof, a nucleic acid, or a combination thereof, as disclosed above.

In specific embodiments, the infectious diseases include but are not limited to virally-mediated, bacterially-mediated, or parasitic diseases currently susceptible to vaccine stimulated protective immune responses or those marginally susceptible with current vaccine technology that could be improved with the current invention. In other embodiments, the non-infectious diseases include but are not limited to cancer by generating similar protective immune responses against known and unknown immunogenic tumor-associated antigens.

In another aspect, the present invention relates to a composition comprising a yeast cell wall particle and silicate, wherein the yeast cell wall particle is modified by "capping" with the silicate. In some embodiments, the composition further comprises an exogenous biological material loaded within the yeast cell wall particle. In other embodiments, a composition encompassed by this invention comprises a yeast cell wall particle loaded with a biological material, and optionally with one or more adjuvants. Preferably, the one or more adjuvants are loaded within the yeast cell wall particle. Additionally, suitable excipients and/or preservatives can be included in the compositions of the invention. It is within the purview of one of ordinary skill in the art to select suitable adjuvants, excipients and/or preservatives. Preferably, the silicate is any organic moiety attached to each of the four oxygen compounds of an orthosilicate, such as tetraethylorthosilicate (TEOS), tetramethylorthosilicate, tetrapropylorthosilicate, or tetrabutylorthosilicate.

In some embodiments, the biological material includes, but is not limited to, a specific protein or a fragment thereof, nucleic acid, carbohydrate, tumor lysate, or a combination thereof. The protein or a fragment thereof, or nucleic acid is selected from the group consisting of a protein, a peptide, an epitope, an antigen, DNA, RNA, cDNA, and an immunogenic fragment or a subunit thereof.

In some embodiments, a small amount of one or more immune response enhancing adjuvants is also loaded within the yeast cell wall particle or administered with the loaded YCWP. The addition of one or more adjuvants to the interior of the YCWP increases the immunogenic effects of the composition. Commonly used adjuvants include, but are not limited to, small molecule compounds, proteins, peptides, nucleic acids and carbohydrates. Suitable adjuvants are those molecules known to mature dendritic cells and interact with receptors on dendritic cells in order to activate dendritic cells and further stimulate a more robust generation of T cells, such as CD4+ and CD8+ T cells. Exemplary adjuvants include, but are not limited to, monophosphoryl lipid A, CpG oligonucleotides (such as CpG DNA), Poly I:C, Poly ICLC, potent WIC II epitope peptides, beta glucan, and dendritic cell stimulating cytokines such as IL-12, IL-15 and IFN-γ, imiquimod, as well as DC maturing cytokines such as IL-4 and GM-CSF.

In one embodiment, the amount of one or more immune response enhancing adjuvants is at least about 10 ng, at least about 50 ng, at least about 100 ng, at least about 200 ng, at least about 300 ng, at least about 400 ng, at least about 500 ng, at least about 600 ng, at least about 700 ng, at least about 800 ng, at least about 900 ng, at least about 1 μg, at least about 5 μg, at least about 10 μg, at least about 15 μg, at least about 20 μg, at least about 25 μg, at least about 30 μg, at least about 35 µg, at least about 40 µg, at least about 45 µg, at least about 50 µg, at least about 60 µg, at least about 70 µg, at least about 80 µg, at least about 80 µg, at least about 90 µg, or at least about 100 µg. In one embodiment, the amount of adjuvant represents between 1-10% (w/w) of the composition. The amount of the adjuvant(s) is sufficient to stimulate receptors, such as the toll-like receptor, on the dendritic cell.

In a related aspect, the present invention relates to a method for preparing a composition comprising a yeast cell wall particle and silicate. The method comprises contacting a yeast cell wall particle with a silicate in the presence of ammonia such that the yeast cell wall particle is "capped" by the silicate. Preferably, the silicate is tetraethylorthosilicate (TEOS), tetramethylorthosilicate, tetrapropylorthosilicate, or tetratbutylorthosilicate.

In another related aspect, the present invention relates to a method for efficient delivery of a biological material to a subject comprising administering to the subject a composition comprising (i) a yeast cell wall particle capped with silicate; and (ii) a biological material loaded within the particle. Preferably, the composition is directly administered to the dermis of the subject such that the dermal dendritic cells phagocytose the loaded particle, thereby triggering the immune response to the biological material. Cells of monocytic origin phagocytose the composition comprising the yeast cell wall particles loaded with a biological material and capped with silicate, thereby promoting differentiation into mature dendritic cells for proper antigen presentation.

In yet another related aspect, the present invention relates to a method for producing a cell mixture containing a yeast cell wall particle loaded with a biological material and capped with a silicate comprising: (i) loading a biological material into a yeast cell wall particle to produce a loaded particle; (ii) capping the loaded particle with a silicate, (iii) freeze-drying the capped, loaded particle; and (iv) incubating the capped, loaded particle with a cell of monocytic origin, such as a pre-dendritic cell, a dendritic cell or a partially differentiated dendritic cell, wherein the incubation causes the cell of monocytic origin to phagocytose the capped, loaded particle. In some embodiments, the cell of monocytic origin is a dendritic cell, and the biological material includes, but is not limited to, a specific protein or a fragment thereof, nucleic acid, carbohydrate, tumor lysate, or a combination thereof.

In specific embodiments, the loading step of the foregoing method for producing an dendritic cell containing a capped, loaded yeast cell wall particle comprises: (a) suspending a yeast cell wall particle and a biological material in a diluent and incubating for a period of time, such as about two hours, to allow the biological material to be absorbed by the yeast cell wall particle and (b) freeze-drying the suspension to load the biological material within the yeast cell wall particle. If necessary, steps (a) and (b) are repeated at least once to increase the loading efficiency.

In specific embodiments, the incubating step of the foregoing method for producing an isolated dendritic cell containing a capped, loaded yeast cell wall particle further comprises: (a) contacting the capped, loaded particle with a dendritic cell at a ratio from about 1:1 to about 100:1, including about 1:1, about 10:1, about 20:1, about 30:1, about 40:1, about 50:1, about 60:1, about 70:1, about 80:1, about 90:1, and about 100:1; (b) incubating the capped, loaded particle with the dendritic cell for 1 to 2 hours and (c) collecting the dendritic cell and washing the cell.

BRIEF DESCRIPTION OF THE DRAWINGS

FIG. 7A shows the structure of tetraethylorthosilicate (TEOS). FIG. 7B shows the partial hydrolysis products of TEOS initiated by the ammonia in the reaction mixture (ethylorthosilicate) forming H-bonds between their OH groups. FIG. 7C shows the silanol condensation product resulting from the loss of water from the H-bonded ethylorthosilicate molecules. This reaction continues in developing polymeric silicates. FIG. 7D structural group shows the similar H-bonding between the polymeric silicate structures and the primary hydroxyl group of the β-glucan bonding between the polymeric silicate structures and the primary hydroxyl group of the β-glucan structure of the yeast cell wall particles. FIG. 7E shows the resulting covalent bond formation between the polymeric silicates and the yeast cell wall particles resulting from this silanol condensation and causing the capping of the loaded yeast cell wall particles.

DETAILED DESCRIPTION OF THE PREFERRED EMBODIMENTS

Figure 1:
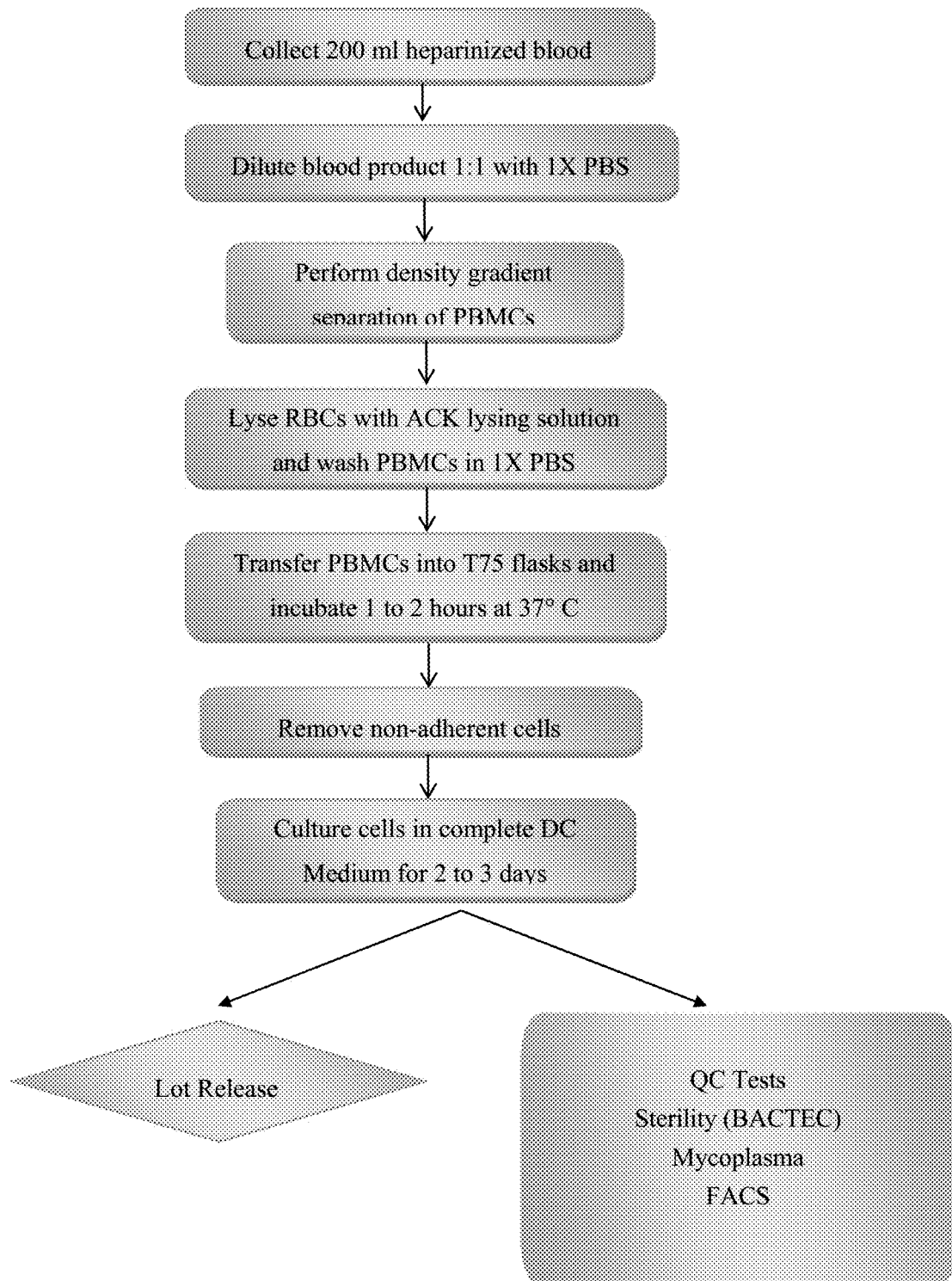
FIG. 1 depicts a process for producing dendritic cells.

Reference is made herein to various methodologies known to those of ordinary skill in the art. Publications and other materials setting forth such known methodologies to which reference is made are incorporated herein by reference in their entireties as though set forth in full.

Definitions

The term "about" in connection with numerical values and ranges means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. For example, "about" means that +/−10% of a particular numerical value following the term.

As used herein "subject" or "patient" denotes any animal in need of treatment with a vaccine. For example, a subject may be suffering from or at risk of developing a condition that can be treated or prevented with a vaccine. As used herein "subject" or "patient" includes humans.

As used herein, the phrases "therapeutically effective amount" and "therapeutic level" mean that the vaccine dosage or plasma concentration of the compositions described herein in a subject, respectively, that provides the specific response for which the biological material or vaccine is administered in a subject in need of such treatment. For convenience only, exemplary dosages, delivery amounts, therapeutically effective amounts and therapeutic levels are provided below with reference to adult human subject. Those skilled in the art can adjust such amounts in accordance with standard practices as needed to treat a specific subject and/or condition/disease.

As used herein, the term "capping" or "capped" means that a polymeric structure, like a "mesh net," covers or coats the yeast cell wall particle such that the biological material loaded within the yeast cell wall particle is retained or entrapped therein. The polymeric structure can be formed by a silicate, such as a tetraalkylorthosilicate.

Vaccine

The term "immunization" means a process by which a subject becomes protected against a particular condition, disease or diseases, usually by receiving a vaccine.

The term "vaccine" is a biological material or product that induces immune response in the body of a subject upon administration, e.g., by injection, by oral administration, or by aerosol administration. Vaccine comprises at least one active component, such as an antigen that induces immune response, and additional components such as adjuvants, conjugates, preservatives, and other excipients including diluents, stabilizers, etc.

Exemplary antigens useful in vaccine applications include allergens, viral antigens, bacterial antigens and antigens derived from parasites. For preventing and treating infectious diseases, bacterial antigens and viral antigens are preferred. Suitable viral antigens include HIV, EBV, HBV, HCV, CMV, and Herpes virus. Additionally, toxins (usually produced by bacteria) can be used as antigens. For non-infectious diseases such as cancer, preferred antigens include tumor associated antigens, with which the artisan will be familiar (e.g., carcinoembryonic antigen, prostate-specific membrane antigen, melanoma antigen, adenocarcinoma antigen, leukemia antigen, lymphoma antigen, sarcoma antigen, MAGE-1, MAGE-2, MART-1, Melan-A, p53, gp 100, antigen associated with colonic carcinoma, antigen associated with breast carcinoma, like HER2 and mammoglobin A, Muc1, Trp-2, telomerase, PSA and antigen associated with renal carcinoma), and can include a combination of antigens or antigenic fragments. In one embodiment, the particle is loaded with tumor cell lysate.

Biological Material

The biological material encompassed by this invention includes, but is not limited to, a specific protein or a fragment thereof, nucleic acid, carbohydrate, tumor lysate, or a combination thereof. One of ordinary skill in the art would understand that fragments of a protein, e.g. a peptide of any length, an epitope, or a subunit of a protein, which produce immunogenic response of a subject upon administration can be used.

In recent years, nucleic acids such as DNA, RNA, cDNA or fragments thereof, are also used as vaccines. In general, the DNA is extracted from an infectious agent's DNA, and then modified/enhanced by genetic engineering before delivering to a subject by electroporation, gene gun, etc.

The biological material of the present invention may be live, wild-type pathogens. Preferably, and antigens are in inactivated or attenuated forms, such as killed viruses, pieces of bacteria, and subunits or immunogenic functional fragments of proteins, polypeptides or nucleic acids. More preferably, the biological material does not cause illness but can effectively provoke an immune response of the subject and protects the subject against future infection of a particular disease.

It is to be understood that yeast cell wall particles have a pore size of at least about 30 nm, and therefore, any molecule/object with a radius of rotation of 30 nm or less can be loaded within the yeast cell wall particles. For example, some viruses or viral particles having a size less than 30 nm (e.g., tobacco mosaic virus) can be loaded within yeast cell wall particles, as well as other antigens, including tumor lysate.

Adjuvants

A number of immune response enhancing agents can be added to the composition as adjuvants to boost immune response such that when the composition is administered to a subject, for example, directly to the dermis of the subject, the immune response is boosted by the adjuvants comparing to administering a composition without any adjuvant. Alternatively, when the composition comprising a biological material loaded particle is incubated with a dendritic cell, the adjuvants exhibit an increased effect on the dendritic cell while dramatically decreasing any systemic effects from such adjuvants. The biological material comprises a protein or a fragment thereof, nucleic acid, carbohydrate, tumor lysate, or a combination thereof.

A number of immune response enhancing agents can be added to the composition for loading within the yeast cell wall particle, as adjuvants to boost immune response such that when the composition is administered to a subject, for example, directly to the dermis of the subject, the immune response is boosted by the adjuvants compared to administering the composition without any additional adjuvants. For example, when the yeast cell wall particles are loaded with a biological material, and the loaded yeast cell wall particle are also incubated with a dendritic cell, and the adjuvants exhibit an increased effect on the dendritic cell while dramatically decreasing any localized or systemic effects from such adjuvants.

It is within the purview of one of ordinary skill in the art to select one or more suitable adjuvants for this invention. For instance, monophosphoryl lipid A, CpG oligonucleotides, Poly I:C, Poly ICLC, potent MHC II epitope peptides, and dendritic cell stimulating cytokines such as IL-12, IL-2, and GM-CSF are good adjuvant candidates of this invention.

Suitable adjuvants are those molecules known to mature dendritic cells and interact with receptors on dendritic cells in order to activate dendritic cells and further stimulate a more robust generation of T cells, such as CD4+ and CD8+ T cells. For instance, monophosphoryl lipid A, CpG oligonucleotides, Poly I:C, Poly ICLC, potent MHC II epitope peptides, and dendritic cell stimulating cytokines such as IL-12, IL-2, and GM-CSF, small molecules such as imiquimod are good adjuvant candidates of this invention.

Particle

As described herein, "particle" refers to any hollow and porous structure that can contain vaccine therein and also allow the vaccine to exit the structure. In some embodiments, the size of the particle is about 0.5 to about 5 µm, which approximates the size of bacterium to allow the particle to be ingested by monocytes, such as dendritic cells. In specific embodiments, the size of the particle is about 0.5 to about 1 µm. In specific embodiments, the size of the particle is about 0.5 to about 2.5 µm. In some embodiments, the particle can be any particle with a glycan network, so long as the particle is about 0.5 to about 5 µm in size.

Preferably, the particle is a digestable or biodegradable particle. In some embodiments, the particle is not limited by a particular shape or material, but can be any shape, size, or material having a hollow or porous structure that allows the particle to be phagocytosed by monocytes, including dendritic cells.

Yeast Cell Wall Particles

In another embodiment, the particle is a yeast cell wall particle YCWP, which is prepared from yeast cell wall such that the particle has a hollow or porous structure to encapsulate a biological material therein. The biological material comprises a protein or a fragment thereof, nucleic acid, or a combination thereof. In one embodiment, the YCWP is prepared from *Saccharomyces cerevisiae*. In another embodiment, the YCWP approximates the size of microbial structures that cells of the mononuclear phagocyte system and other phagocytic cells typically ingest. In specific embodiments, the YCWP is about 1-25 µm, preferably 1-5 µm, 5-10 µm, 10-15 µm, 15-20 µm, 15-25 µm, or 20-25 µm. For example, the YCWP is about 20 µm.

In one embodiment, the YCWP is prepared by (a) suspending yeast to produce a suspension, (b) incubating the suspension, (c) centrifuging the suspension and removing the supernatant and (d) recovering the resulting YCWP. In another embodiment, steps (a)-(d) are repeated at least 1, 2, 3 or 4 times.

In another embodiment, the YCWP is prepared by (a) suspending yeast in a solution to produce a first suspension, (b) incubating the first suspension, (c) centrifuging the first suspension and removing the supernatant, (d) suspending the resulting pellet to produce a second suspension, (e) incubating the second suspension, (f) centrifuging the second suspension and removing the supernatant and (g) washing the resulting pellet to recover the YCWP. In another embodiment, the YCWP is sterilized.

In specific embodiments, the yeast is suspended in NaOH, including 1M NaOH. In specific embodiments, the first suspension is incubated at about 80° C. for about 1 hour or for 1 hour. In specific embodiments, the centrifuging is performed at about 2000 times gravity for about 10 minutes, or at 2000 times gravity for 10 minutes. In specific embodiments, the pellet is suspended in water, including water at about pH 4.5 or at pH 4.5. In specific embodiments, the second suspension is incubated at about 55° C. for about 1 hour or at 55° C. for 1 hour. In specific embodiments, the pellet is washed in water at least 1, 2, 3 or 4 times. In specific embodiments, the pellet is washed once.

In another embodiment, the YCWP is sterilized using isopropanol and/or acetone following washing of the pellet. In specific embodiments, other known alcohols are appropriate. In specific embodiments, the YCWP is allowed to fully dry after sterilization. In another embodiment, the YCWP is resuspended after being allowed to dry. In specific embodiments, the YCWP is resuspended in PBS, such as 1×PBS.

In another embodiment, the YCWP is allowed to dry and then to be frozen before the biological material is loaded into the YCWP and/or before capped with silicate, in order to place the YCWP in storage before use. In specific embodiments, the YCWP is freeze dried and stored at about 4° C. or lower. In specific embodiments, the YCWP is freeze dried and stored at 4° C. The biological material comprises a specific protein or a fragment thereof, nucleic acid, carbohydrate, tumor lysate, or a combination thereof.

Biological Material Loaded Particle

The particle, for example, the yeast cell wall particle, is loaded with a biological material, such as a specific protein or a fragment thereof, nucleic acid, carbohydrate, tumor lysate, or a combination thereof. In one embodiment, the biological material is loaded into the particle by incubating the biological material and a suspension of particle, for example, the yeast cell wall particles together and allowing the biological material to penetrate into the hollow insides of the particles.

In another embodiment, after the particle or the yeast cell wall particle is incubated or loaded with the biological material, the combination is freeze-dried to create an anhydrous vaccine within the particle. By freeze-drying, the biological material is trapped within the particle and ready to be phagocytosed by a monocyte, such as a dendritic cell. In specific embodiments, the freeze-drying is the only mechanism used to trap the biological material within the particle. In specific embodiments, the entrapment is not caused by a separate component blocking the biological material from exiting the particle, for example, by physical entrapment, hydrophobic binding, any other binding. In specific embodiments, the entrapment is not caused by crosslinking or otherwise attaching the biological material to the particle outside of any attachment that may occur upon freeze-drying. In specific embodiments, the compositions of the present invention do not include any additional component that specifically assists in evading the lysosome. The biological material includes, for example, a specific protein or a fragment thereof, nucleic acid, carbohydrate, tumor lysate, or a combination thereof.

In another embodiment, the biological material is incorporated into the yeast cell wall particle. In specific embodiments, the number of YCWPs is about $1 \times 10^9$ and the volume of biological material is about 50 µL. In specific embodiments, the incubation is for about one hour or less than one hour at about 4° C. In some embodiments, the combination of YCWPs and biological material is freeze dried over a period of less than or about 2 hours.

Figures 7A, 7B, 7C, 7D, 7E:
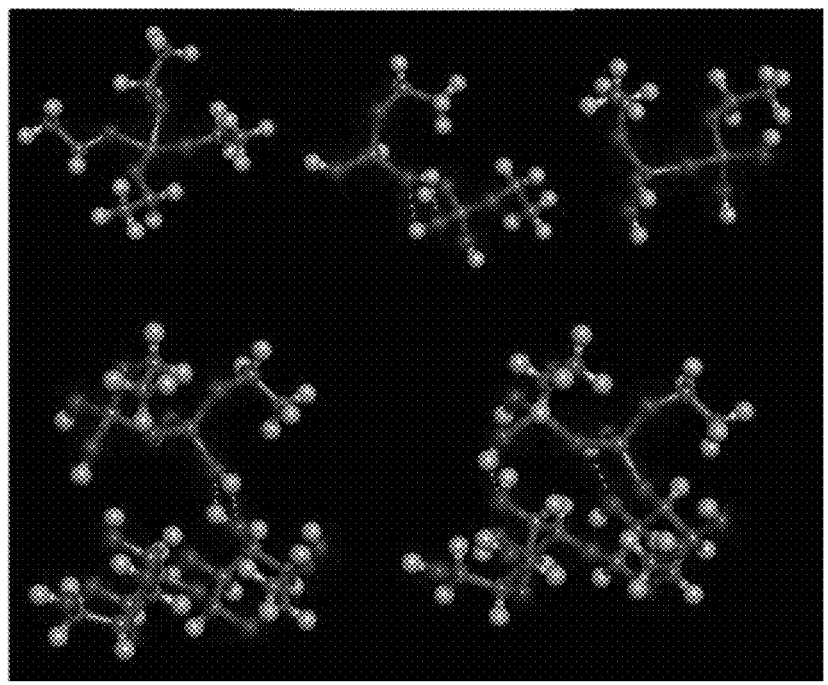
FIGS. 7A-7E depict the structure of the silicate capped yeast cell wall particles. Silicon is depicted in the darker grey color while the lighter grey color represents carbon.

In another embodiment, the loaded yeast cell wall particle is capped with a silicate. Specifically, in some embodiments the loaded YCWPs are capped by contacting the YCWPs with a silicate, such as tetraalkylorthosilicate, in the presence of ammonia, such that the loaded YCWPs are capped with the silicate. In preferred embodiments, the loaded YCWPs are capped with the silicate within about 60 minutes, about 45 minutes, about 30 minutes, about 15 minutes, about 10 minutes, about 5 minutes or about 2 minutes. The reactivity of the tetraalkylorthosilicates is such that under hydrolysis mediated by the ammonia, the tetraalkylorthosilicates react with the primary hydroxyls of the β-glucan structure of the YCWPs. The tetraalkylorthosilicates also self-react with the ends of these cell wall silicates to form "bridges" such as —O—Si(OH)$_2$—O— or in three dimensions such as —O—Si(—O—Si—O—)(OH)—O— or —Si (—O—Si—O—)$_2$—O—. These bridges may occur across the pores in the YCWPs such that the retention of the loaded drug or biological material therein is increased. The structure of the capped YCWPs is depicted in FIG. 7E. Such a capped, loaded YCWP can be freeze dried.

The inventor of the present application unexpectedly discovered that loaded YCWPs capped with silicate are an effective vaccine delivery system. More specifically, the capped YCWPs retain more loaded material than the uncapped YCWPs. Even more surprisingly, the capped YCWPs not only deliver significantly more released biological material into the cytoplasm of the phagocytic cells but also deliver significantly more loaded particles into the phagocytic cells in comparison to the uncapped YCWPs, as detailed in the working examples.

In another embodiment, the loaded particle is resuspended in a diluent or solution after the freeze-drying. In specific embodiments, the diluent or solution is water. In specific embodiments, the loaded particle is resuspended and/or incubated with additional biological material, for example, vaccine, to penetrate the particle and the combination is then freeze-dried again. In other embodiments, the combination is subjected to multiple freeze-drying and resuspensions. In other embodiments, the biological material loaded particle is sterilized in ethanol after the freeze-drying and before use. The biological material includes, for example, a protein or a fragment thereof, nucleic acid, carbohydrate, tumor lysate, or a combination thereof.

In specific embodiments, the biological material is loaded into the particle by (a) incubating the biological material and a suspension of the particles, allowing the biological particle to penetrate into the hollow insides of the particles and freeze-drying the suspension of loaded particle and (b) optionally resuspending the particles, incubating the resuspended particles and freeze drying the resuspended particles and any vaccine not already in the particle.

In specific embodiments using YCWPs, the number of YCWPs is about 1×10$^9$ and the volume of the biological material is about 50 μL. In specific embodiments, the number of YCWPs is 1×10$^9$ and the volume of the biological material is 50 μL. In specific embodiments, the incubation in step (a) is for less than one hour at about 4° C. In specific embodiments, the incubation in step (a) is for about one hour at 4° C. In some embodiments, the foregoing suspension is freeze dried in step (a) over a period of less than 2 hours or over a period of about 2 hours. In some embodiments, the YCWPs in step (b) are resuspended in water, including about 50 μL of water or 50 μL of water. In some embodiments, the resuspended YCWPs are incubated in step (b) for less than or about one hour at about 4° C. or for less than or about 2 hours at 4° C. The biological material includes a specific protein or a fragment thereof, nucleic acid, carbohydrate, tumor lysate, or a combination thereof.

Prior to administration, the capped, loaded yeast cell wall particle is resuspended in a pharmaceutically acceptable excipient, such as PBS or a saline solution.

Dendritic Cell

As described herein, "dendritic cell" refers to a cell generated from a peripheral blood mononuclear cell ("PBMC"). In one embodiment, a dendritic cell is prepared by (a) collecting blood, (b) diluting the blood, (c) performing a density gradient separation of PBMCs, (d) lysing red blood cells and washing the PBMCs, (e) incubating the PBMCs, (f) removing nonadherent cells and (g) culturing adherent cells in media.

In some embodiments, the dendritic cell is an immature dendritic cell that has been cultured for no more than 5 days. In other embodiments, the dendritic cell has been cultured for 6-8 days.

In specific embodiments, the blood is heparinized. In specific embodiments, the density gradient separation at step (c) comprises placing the blood in a Lymphocyte Separation Medium and then centrifuging the blood. In specific embodiments, the centrifuging is performed at about 1000 times gravity for about 20 minutes or at 1000 times gravity for 20 minutes. In specific embodiments, a second centrifuging is performed before step (d) and is performed at about 500 g for about 5 minutes or is performed at 500 g for 5 minutes. In specific embodiments, a third centrifuging is performed before step (d) and is performed at about 500 g for about 10 minutes or is performed at 500 g for 10 minutes. In specific embodiments, the centrifuging is performed at about 1200 times gravity for about 10 minutes or at 1200 times gravity for about 15 minutes. In specific embodiments, a second centrifuging is performed before step (d) and is performed at about 500 g for about 5 minutes or is performed at 500 g for 5 minutes. In specific embodiments, the lysing is performed using an ACK lysing solution, followed by incubation, preferably at room temperature for about 5 minutes, and followed by a subsequent centrifugation. In specific embodiments, the PBMCs are washed in RPMI medium. In specific embodiments, the PBMCs are incubated at step (e) in flasks at about 37° C. for about 1-2 hours or at 37° C. for 1-2 hours. In specific embodiments, serum-free DC media is added to the flask.

In some embodiments, one or more cytokines is present in the culture media, including, but not limited to, granulocyte macrophage colony stimulating factor (e.g., 800 units/ml) and IL-4 (e.g., 500 units/ml).

Vaccine Compositions

In some embodiments, the biological material loaded particles are directly injected into the dermis of a subject such that the loaded particles are phagocytosed by dermal dendritic cells. In some embodiments, optionally, the biological material loaded particle is in vitro phagocytosed within a monocyte, preferably a dendritic cell. In some embodiments, the yeast cell wall particles loaded with a biological material and capped with silicate are directly injected into the dermis of a subject such that the particles are phagocytosed by dermal dendritic cells. In one embodiment, the biological material loaded particle is incubated with a dendritic cell such that the cell phagocytoses the biological material loaded particle. The biological material includes, for example, a specific protein or a fragment thereof, nucleic acid, carbohydrate, tumor lysate, or a combination thereof. In other embodiments, the capped, loaded particles are phagocytosed by a monocyte in vitro, wherein the monocyte is preferably a dendritic cell.

In specific embodiments, the particle is incubated with the dendritic cell at a ratio of from about 1:1 to about 100:1, optionally prior to human administration. The incubation can be performed for about 1 hour, 1 hour or preferably less than 1 hour.

In specific embodiments, the dendritic cell containing the capped, loaded particle is collected and washed, for example, at least 1, 2, 3 or 4 times. In other embodiments, the dendritic cells are incubated after washing, resuspended in freezing medium, and frozen for storage before use. In specific embodiments, the resuspension produces a concentration of about 10×10$^6$ cells per ml or 10×10$^6$ cells per ml. In specific embodiments, the resuspension is frozen for storage before use.

Formulation

The compositions of the present invention may be formulated for mucosal administration (e.g., intranasal and inhalational administration) or for percutaneous administration. The composition of the invention can also be formulated for parenteral administration (e.g., intramuscular, intravenous, or subcutaneous injection), and injected directly into the patient and target cells of monocytic origin, like macrophages and dendritic cells. In specific embodiments, the capped, biological material loaded particles without prior incubation with dendritic cells are directly injected into the dermis of a subject. Thus, the compositions of the present invention may be administered just like a conventional vaccine. This also substantially reduces cost because of the lower level of skill required In other embodiments, the capped, loaded particle is first incubated with cells of monocytic origin, such as dendritic cells, prior to administration to a subject.

Formulations for injection may be presented in unit dosage form, e.g., in ampules or in multi-dose containers, optionally with an added preservative. The compositions may take such forms as suspensions, solutions or emulsions in oily or aqueous vehicles, and may contain formulatory agents such as suspending, stabilizing and/or dispersing agents. The composition of the present invention may also be formulated using a pharmaceutically acceptable excipient. Such excipients are well known in the art, but typically will be a physiologically tolerable aqueous solution. Physiologically tolerable solutions are those which are essentially non-toxic. Preferred excipients will either be inert or enhancing, but a suppressive compound may also be used to achieve a tolerogenic response. Alternatively, the composition is not administered with any other immunosuppressive treatment, such as steroids or chemotherapy.

Therapeutic Methods

The compositions of the present invention attract phagocytic cells, such as cells of the mononuclear phagocyte system, including monocytes, macrophages, dendritic cells or immature dendritic cells and therefore can be used as a vaccine. In the field of vaccination, cells of the mononuclear phagocyte system are considered "professional" antigen presenting cells and thus, are the ideal target for vaccine delivery. It is well known that presentation of an antigen within an APC is vastly more effective in generating a strong cellular immune response than expression of this same antigen within any other cell type. Therefore, the ability of the compositions of the present invention to present an antigen on an antigen presenting cell via class I MHC and class II MHC molecules dramatically enhances the efficacy of such a vaccine.

The present invention contemplates both prophylactic and therapeutic uses of the compositions disclosed herein for infectious diseases such as virally-mediated, bacterially-mediated, and parasitic diseases currently targeted with vaccine strategies or those marginally susceptible due to limitations of current vaccine technology, and noninfectious diseases, including cancer. The disease to be treated is not particularly limiting, but depends on the biological material loaded into the particle. Such exemplary biological material includes a tumor lysate, protein or a fragment thereof, nucleic acid, carbohydrate, or a combination thereof.

The compositions of the present invention come into contact with phagocytic cells either in vivo or in vitro. Hence, both in vivo and in vitro methods are contemplated. As for in vivo methods, the compositions of the present invention are generally administered parenterally, usually intravenously, intramuscularly, subcutaneously, interdermally or intradermally. They may be administered, e.g., by bolus injection or continuous infusion. In in vitro methods, monocytic cells are contacted outside the body and the contacted cells are then parenterally administered to the patient.

Dosage

In some embodiments, about 200 µL of a $10 \times 10^6$ concentration of dendritic cells containing biological material locaded particles, or capped, biological material loaded yeast cell wall particles forms one dose of the treatment. In another embodiment, the dose is administered by diluting the 200 µL aliquot to a final volume of 1 ml before administering the dose to a subject. In specific embodiments, the aliquot is diluted with sterile saline containing 5% human serum albumin. In specific embodiments, the 200 µL aliquot will need to be thawed before dilution. In such a scenario, the length of time between thawing and administration of the dose to a subject will be no longer than 2 hours. In some embodiments, the diluted aliquot is administered in a 3 cc syringe. In some embodiments, a syringe needle no smaller than 23 gauge is used.

In another embodiment, a subject is administered at least 1, 2, 3 or 4 doses of the compositions of the present invention. In specific embodiments, a subject is re-vaccinated once every 4 weeks. In some embodiments, the composition comprising biological material loaded particle is administered to a subject without first fusing to dendritic cells. In specific embodiments, a subject is re-administered with the composition once every 4 weeks. In specific embodiments, about 1-2 million dendritic cells containing the biological material loaded particles or the capped, loaded particles is administered optionally by injection at each vaccination. In specific embodiments, the biological material loaded particles or capped, loaded particles are injected in a subject at or near (1) a site of infection or disease, or (2) a lymph node. The biological material includes, for example, a protein or a fragment thereof, nucleic acid, or a combination thereof.

The vaccine composition can also contain biological adjuvants, including but not limited to nucleic acids such as CpG oligonucleotides, proteins or peptide epitopes such as the tetanus toxoid MHC class II-binding p30 peptide.

The present invention is further illustrated by the following working examples, which are for illustration purpose only and by no means limiting the scope of the present invention.

EXAMPLES

Example 1: Preparing Dendritic Cells

Dendritic cells were generated from a patient's PBMCs. PBMCs were collected from the patient by a blood draw of 200 ml following standard operating procedures. The blood was then transferred to 250 ml centrifuge tubes and diluted 1:1 with 1×PBS. Then, 35 ml of the diluted blood was layered over 15 ml of room temperature Lymphocyte Separation Medium (LSM; Mediatech) in 50 ml tubes and centrifuged at 1000 g for 20 minutes at room temperature. The PBMC layers were removed by pipetting from the LSM gradients and placed into clean 50 ml centrifuge tubes. Four volumes of 1×PBS were added and the tubes were inverted to mix the contents. The PBMCs were then centrifuged at 500 g at room temperature for 5 minutes. Ten ml of 1×PBS were added into each tube and the cells were resuspended and pooled into 1 tube. The PBMCs were again centrifuged at 500 g at room temperature for 10 minutes, resuspended in 20 to 40 ml of ACK lysing solution (Cambrex) and incubated at room temperature for 5 minutes. The cells were then centrifuged again at 1500 rpm for 5 minutes. The PBMCs were resuspended in 30 ml RPMI-1640 medium (Mediatech). The cells were then transferred into 2-4 T75 flasks. The flasks were incubated at 37° C. for 1 to 2 hours. The non-adherent cells were then removed by rinsing. Afterwards, 10 ml of 1×PBS were added into each flask, the flask swirled, and the PBS removed. Afterwards, 10 ml of complete DC media (serum-free DC Medium+800 U/ml GM-CSF+1000 U/ml IL-4) was added to each flask. The flasks were then incubated at 37° C., 5% CO2 for 2 days. On Day 3, 10 ml of complete DC medium was added into each flask. The cells were then incubated for another 2 days. On Day 6 or 7, the resulting immature dendritic cells were ready for use.

FIG. 1 provides an overview of the generation of dendritic cells.

Example 2: Preparing the Antigen

Synthetic antigens such as peptides can be easily produced commercially and provided in lyophilized state. These peptides can be re-constituted and co-incubated with the prepared YCWP for loading. Similarly, recombinant proteins and/or isolated proteins can be suspended in solution and co-incubated with the YCWP for loading as discussed below.

Example 3: Preparing Tumor Lysate

A tumor sample was obtained from a patient. After separating fat and necrotic tissue away from the tumor tissue, the tissue was weighed and 1×PBS added (50 µL of PBS per 200 µg of tissue) and the tumor was minced thoroughly with scalpels in 1×PBS. The tumor cells were then subjected to 4 cycles of freeze and thaw. The freezing was performed in liquid nitrogen for 20 minutes and the thawing was performed at room temperature. Prepared tumor lysate was quantified by a spectrophotometer. An aliquot was taken for quality control testing. The remainder was stored at ≤−135° C. in preparation for vaccine preparation. Small amounts of adjuvant can optionally be added after the freeze thaw cycles.

Figure 2:
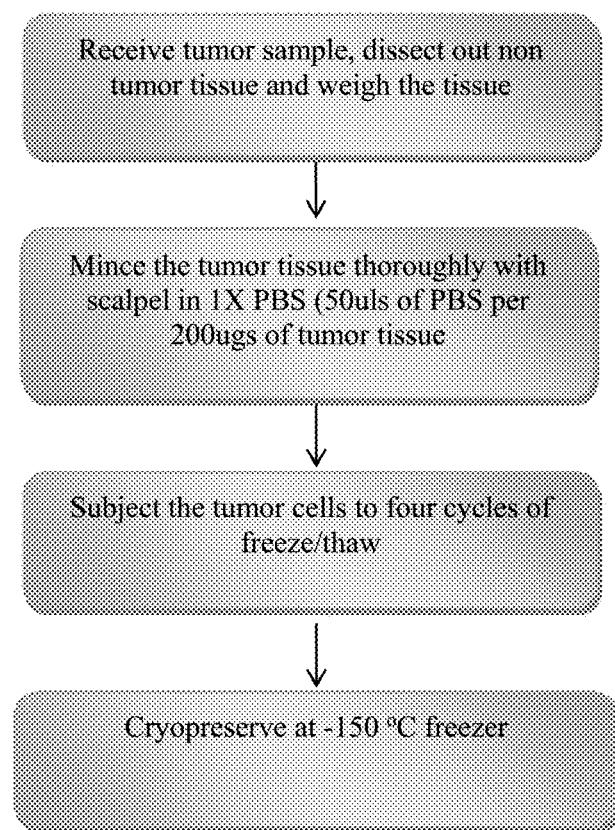
FIG. 2 depicts a process for producing tumor lysate.

FIG. 2 provides an overview of the tumor cell lysate processing.

Example 4: Preparing Yeast Cell Wall Particles

YCWPs were prepared from Fleishmans Baker's Yeast or equivalent. Briefly, 10 g of Fleishmans Baker's yeast was suspended in 100 ml of 1 M NaOH and heated to 80° C. for one hour. The undissolved yeast cell walls were recovered by centrifugation at 2000×g for 10 minutes. The recovered yeast cell walls were then resuspended in 100 ml of water with the pH adjusted to 4.5 with HCl and incubated at 55° C. for an additional hour, and subsequently recovered by centrifugation. The recovered YCWPs were then washed with water once, isopropanol 4 times and finally acetone 2 times. Once the YCWPs were fully dried they were resuspended in PBS, counted, aliquoted into groups of $1 \times 10^9$ particles and freeze dried for use in manufacturing the vaccine.

Figure 3:
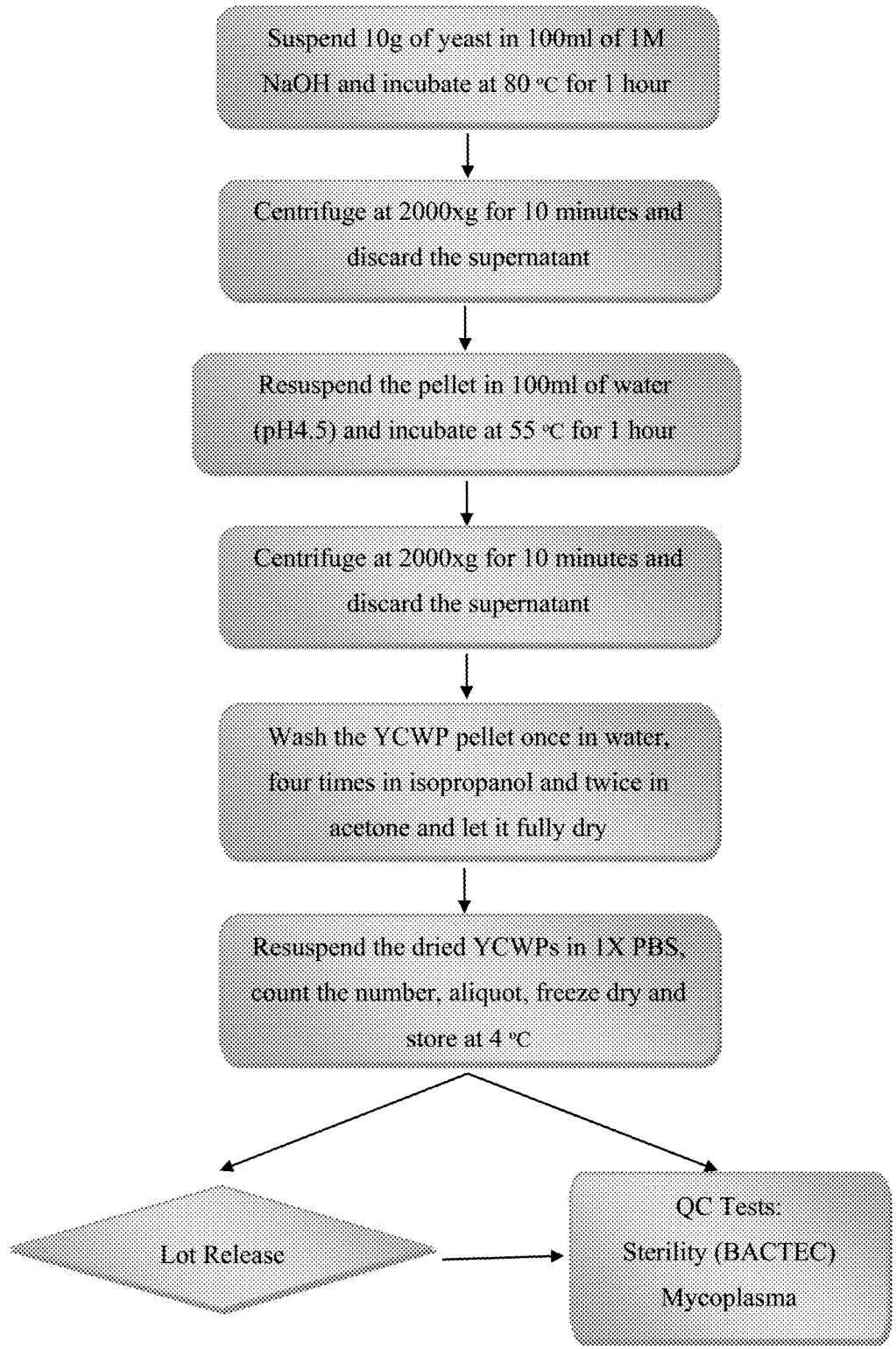
FIG. 3 depicts a process for producing yeast cell wall particles.

FIG. 3 provides an overview of the yeast cell wall particles processing.

Example 5: Preparing Yeast Cell Wall Particles

Three grams of active dry yeast (Fleischmann's or equivalent) were washed three times in water by suspending the yeast in 30 mL of sterile water, vortexing, and centrifuging at 800-1000×g for 5 minutes at room temperature. After decanting the supernatant, the yeast pellet was resuspended in 50 mL of 1 M NaOH and heated in a 90° C. water bath for 1 hour.

The yeast suspension was subsequently centrifuged at 800-1000×g for 5 minutes, and the pellet was resuspended in 25-30 mL of acid water (pH adjusted to 4.5 with HCl). The acid water wash step was repeated until the pH of the suspension is <7.0. Then the pellet was resuspended in 30 mL acid water and incubated in a 75° C. water bath for 1 hour. The yeast pellet was recovered by centrifugation at 1000×g for 5 minutes, and then washed with 10 mL of sterile water 3 times, 10 mL of isopropanol 4 times and finally 10 mL of acetone 2 times. The acetone was carefully removed, and the pellet was spread evenly on the glass surface of a beaker, allowed to air dry overnight.

The dried YWCPs were collected and stored in a vacuum jar at 4° C. and then washed in 10-15 mL of filtered 70% ethanol 3 times. The YWCPs were briefly sonicated on the final wash, and the sonication was repeated if necessary to disperse clumps. Once the ethanol was removed, the YWCPs were washed in sterile water. Aliquots of 100 µl of YWCPs were dispensed into 2.0 mL rounded bottom snap top centrifuge tubes, placed in freezer for 1 hour, freeze dried, and stored in a vacuum jar at 4° C. for future use.

Example 6: Preparing Yeast Cell Wall Particles

Yeast cell wall particles (YCWPs) were prepared by suspending *Sacharomyces cerevisiae* (100 g of Fleishmans Bakers yeast, AB Mauri Food Inc., Chesterfield, Mo.) in 1 L of 1 M NaOH and heating to 80° C. for 1 h. The insoluble material containing the yeast cell walls was collected by centrifugation at 2000×g for 10 min. This insoluble material was then suspended in 1 L of water, brought to pH 4-5 with HCl, then incubated at 55° C. for 1 h. The insoluble residue was again collected by centrifugation and washed once with 1 L of water, four times with 200 mL of isopropanol, and twice with 200 mL of acetone. The resulting slurry was dried at room temperature in a sterile hood to produce 12.4 g of a fine, slightly off-white powder. The powder composed of dry YCWPs was carefully weighed and suspended in sterile distilled water at a concentration of 10 mgs/ml, 1 ml aliquots were placed in sterile Eppendorf tubes, frozen at −60° C. and freeze dried at 0.012 mBar. Because the boiling point of isopropanol and acetone is considerably below that of water, any possible contamination by these solvents would be removed under these high vacuum conditions.

Example 7: Preparing Tumor Lysate and Loading YCWPs

Tumor protein antigens are released from tumor tissue by three freeze (−60° C.)/thaw cycles followed by centrifugation at 21,000 g to remove all non-soluble material. The soluble tumor antigenic material and optionally included adjuvant material is loaded into the inside of the hollow YCWPs by two hours of incubation at 4° C. to allow the small volume of soluble tumor lysate to fully penetrate the hollow insides of the YCWPs. The volume of soluble tumor lysate used is carefully calculated to closely approximate the volume of the insides of the YCWPs such that the vast majority of the soluble tumor lysate, after incubation, resides within the hollow insides of the YCWPs. Following incubation the fully solvated YCWPs are frozen at −60° C. and all water removed by freeze drying at 0.012 mBar vacuum for 8 hours leaving the anhydrous tumor lysate antigenic material mostly inside the hollow YCWPs. In order to drive any residual tumor lysate material into the insides of the YCWPs the same tiny calculated volume of the insides of the YCWPs of sterile water is added to the dried partially loaded YCWPs and again incubated for two hours at 4° C., followed again by freeze drying at 0.012 mBar vacuum for 8 hours.

Example 8: Loading Biological Material into YCWPs

Figure 4:
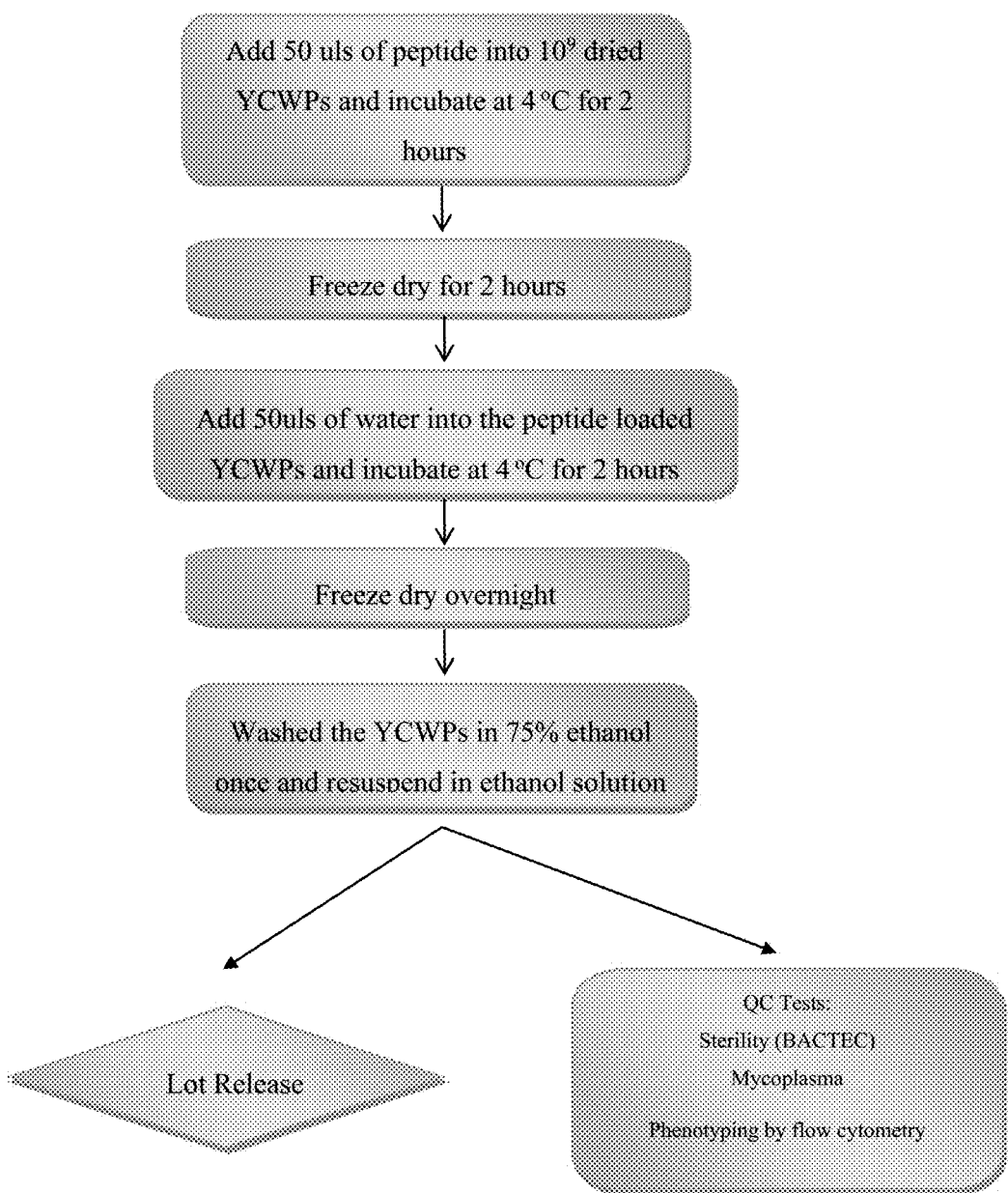
FIG. 4 depicts a process for loading biological material into yeast cell wall particles.
Figure 5:
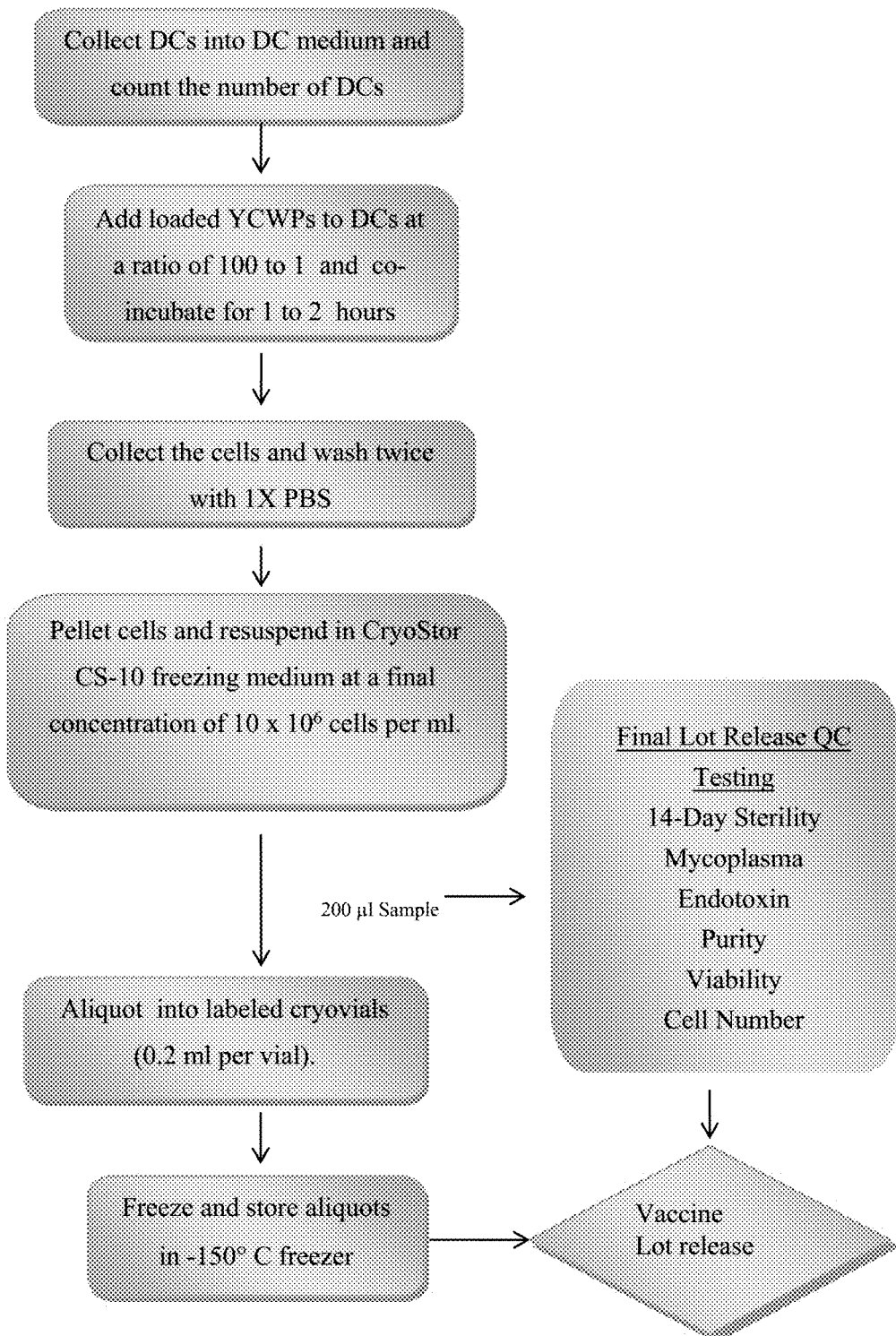
FIG. 5 depicts a process for producing vaccine particle loaded dendritic cells.

A suspension of fully anhydrous YCWPs ($1\times10^9$) is placed in contact with 50 µL of a peptide in PBS over a period of 2 hours at 4° C., allowing the peptide to penetrate into the hollow insides of the YCWPs to produce loaded YCWPs. The suspension is then freeze dried for 2 hours. After freeze drying, 50 µL of water is added to the loaded YCWPs, incubated for another 2 hours at 4° C. and again freeze dried to yield YCWPs with dry biological material within their hollow insides. The loaded YCWPs are then sterilized by washing in ethanol and maintained in ethanol. FIG. 4 provides an overview of the YCWPs loading procedure.

Example 9: Loading YCWPs with Tumor Lysate

A patient tumor biopsy sample was mixed carefully with 50-100 µl of lysis buffer (PBS) (depending on the amount of the tumor sample), avoiding bubbles during mixing, and was then incubated at 4° C. for 30 minutes. The mixture was subjected to freeze-thaw 3 times in acetone-dry ice bath and 37° C. water bath, and centrifuged at 4° C. for 10 minutes at maximum speed. 50 µl of the prepared tumor lysate was added in a sterile 2 mL centrifuge tube containing 10 mg of dried YCWPs such that the liquid tumor lysate covered the YCWPs. The mixture was incubated at 4° C. for 2 hours until the liquid tumor lysate soaked into the YCWPs.

The tube was then placed into a −85° C. freezer for 30 minutes for a quick freeze of the pellet. The tube was placed on freeze drier overnight. 50 µl of sterile water was added onto the dried yeast pellet and incubated at 4° C. for 2 hours to allow the liquid to soak into the pellets.

The tube was placed into a −85° C. freezer for 30 minutes for a quick freeze of the pellet. The tube was then placed on freeze drier overnight. The dried particles were then resuspended in 1 mL of 70% ethanol and stored at 4° C. for future use.

Example 10: Administering Loaded YCWPs to Subject

The loaded YCWPs prepared according to Examples above are resuspended in 1 mL of a solution suitable for injection, such as sterile water for injection or sterile saline for injection, which optionally contains 5% human serum albumin, under sterile conditions. Once the loaded YCWPs are carefully resuspended, the entire volume is drawn and injected to the dermis of a patient using a syringe.

Example 11: Preparing Dendritic Cells Containing Loaded Particles

The loaded YCWPs prepared according to Examples above in 70% ethanol suspension are centrifuged. The ethanol is removed carefully and replaced with 1 mL of PBS. The loaded YCWPs are sonicated. The loaded YCWPs are washed with sterile 1×PBS. After final wash, the loaded YCWPs are resuspended in PBS to approximately $1\times10^8$ particles/100 µl PBS.

The loaded YCWPs are added to a dendritic cell culture at a ratio of 1:100, and the culture was returned to 37° C. incubator. Subsequently, the following factors are added to the culture: 50 µg/mL of TNF-α in sterile water is added to the culture at a ratio of 1:5000 in volume (2 µL per 10 mL of culture); 10 µg/mL of IL-1β in sterile water is added to the culture at a ratio of 1:1000 in volume; 10 µg/mL of IL-6 in sterile water is added to the culture at a ratio of 1:1000 in volume; and 1 mg/mL of PGE2 in 100% ethanol is added to the culture at a ratio of 1:1000 in volume. After all factors are added and mixed into the culture, the culture is incubated overnight.

Example 12: Harvest of Dendritic Cells, Preparation and Cryopreservation of Vaccine Composition The dendritic cell culture prepared according to Example 11 was removed from the incubator. The following procedure was performed in a hood under sterile conditions. 10 mL of media were removed from culture flask. The culture flask was rinsed with 4.0-4.5 mL of 1×PBS and also added to the media.

1.5-2.0 mL of CellStripper™ was added to the culture flask. The culture flask was placed in 37° C. incubator for 10-20 minutes. About 4 mL of the culture media were added back to the flask from the tube to wash and remove cells. The flask was washed to harvest as many cells as possible. The cells were counted on hemacytometer or Cellometer™. The supernatant was removed after centrifugation.

Subsequently, the cells were resuspended in CryoStor™ 10 at $5\times10^6$ cells/mL, aliquoted into cryovials properly labeled with patient ID Number, date and cell concentration at $1.25\times10^6$ cells/mL per vial (about 250 µL). A 250-500 µL portion was saved in a cryovial for sterility testing, and the remaining vials were stored in Styrofoam containers and placed under −86° C. to step down freeze.

Example 13: Preparation of the Solid Dose of Vaccine for Patient Administration

One cryovial of patient's cell was removed from cryostorage and carefully thawed at 37° C. in a water bath. Under sterile conditions, 1 mL of sterile saline for injection with 5% human serum albumin (or 1 mL of sterile 1×PBS) was gently added to the cryovial containing the cells. After the cells were carefully resuspended, the entire volume from the cryovial was drawn and the syringe containing the vaccine was used for administration to a patient.

Example 14: Immunization Procedure

To vaccinate a subject, a dose of 1.25 million dendritic cells containing vaccine loaded particles is cryopreserved in 0.2 mL of a serum-free, 10% dimethyl sulfoxide freezing medium (CryoStor™ CS-10, BioLife Solutinos, Inc.). Before injection, the dendritic cells is thawed and diluted to a 1 mL with sterile saline for injection containing 5% human serum albumin (Albuminar −25, Aventis Behring). The dilution is then transferred to a 3.0 cc syringe for injection and using a needle no smaller than 23 gauge, which is administered within 2 hours of the thawing. The injection can be administered subcutaneously into an area of lymph nodes or administered intradermally.

Example 15: Isolation of Mononuclear Cells from Whole Peripheral Blood Using the SepMate-50 System Sepmate-50 tubes with inserts allow for quickly layering diluted blood over the density gradient medium (LSM), and prevents the layers from mixing. After centrifugation with the brake on, enriched peripheral blood mononuclear cells (PBMC's) are poured into a fresh tube and processed as described below for future culturing Procedure 1:

| STEP | PROCEDURE/WORK INSTRUCTIONS |
|---|---|
| 1 | Add 15 mL of lymphocyte separation medium (LSM) to each SepMate tube by carefully, yet quickly, pipetting it through the central hole of each tube insert. |
| 2 | Pool the whole blood. |
| 3 | Dilute the whole blood sample with twice the initial blood volume of 1xPBS. |
| 4 | Add 30 mL diluted blood to the Sepmate tubes. |
| 5 | Centrifuge for 10-15 minutes at room temperature. |
| 6 | Pour off the top layer containing the enriched PBMC's from each Sepmate tube into new centrifuge tubes. |
| 7 | Cap tubes and centrifuge 5 minutes. |
| 8 | Resuspend pellet in each tube with up to 1.0 mL ACK lysing buffer with pipette. Repeat cycles of adding 1X PBS to resuspend pellet and centrifuge. |
| 9 | Decant the supernatant, and aliquot $50 \times 10^6$ cells suspended in 15 mL RPMI media per flask. Place in the $CO_2$ incubator at 37° C. for 1-1.5 hours. |
| 10 | Remove flasks from incubator. Wash pellet with 1X PBS. |
| 11 | Add 15 mL complete DC Media (containing IL-4, GM-CSF, and Gentamycin) and place in the 37° $CO_2$ incubator for 22-24 hours. |
| 12 | On Day 2, continue with inoculation of cultures with YWCP's and cytokines after the dendritic cells have incubated at 37° C. for approx. 22 hours. |

Procedure 2:

| STEP | PROCEDURE/WORK INSTRUCTIONS |
|---|---|
| 1 | Add 15 mL of lymphocyte separation medium (LSM) to each SepMate-50 tube by carefully, yet quickly, pipetting it through the central hole of each tube insert. |
| 2 | Pool the whole blood into a sterile 500 mL bottle or sterile 250 mL conical tubes. |
| 3 | Dilute the whole blood sample with twice the initial blood volume of 1xPBS in the sterile 500 mL flask, and mix gently. |
| 4 | Add 30 mL diluted blood by pipetting it smoothly and quickly down the side of the Sepmate-50 tubes. |
| 5 | Centrifuge at 1200 g for 10-15 minutes at room temperature with the brake on. |
| 6 | Pour off the top layer containing the enriched PBMC's from each Sepmate tube into new sterile 50 mL centrifuge tubes. |
| 7 | Cap tubes and centrifuge at 500 g for 5 minutes with brake on. |
| 8 | Decant supernatant into waste bottle and resuspend pellet in each tube with up to 1.0 mL ACK lysing buffer with pipette. |
| 9 | Combine into two sterile 50 mL tubes containing 5 mL of cell suspension each, and add 5-10 mL 1xPBS to each tube. |
| 10 | Centrifuge again at 500 g for 5 minutes with brake on. Decant the supernatant and resuspend the pellets with pipette in 10 mL 1xPBS. |
| 11 | Bring total volume in the tube(s) to 50 mL with 1xPBS |
| 12 | Centrifuge at 200 g for 10 minutes with brake on. |
| 13 | Decant supernatant into waste bottle, and resuspend pellet in 1xPBS up to the 50 mL demarcation on the tube, cap and mix well. |
| 14 | Remove an amount of the well-mixed suspension sufficient to perform a cell count, and record. |
| 15 | Centrifuge again at 200 g for 10 minutes with brake on. |
| 16 | Decant the supernatant, and aliquot $50 \times 10^6$ cells suspended in 15 mL RPMI media per flask. |
| 17 | Label the cell culture flasks with the patient ID, date, and initials and place in the $CO_2$ incubator at 37° C. for 1-1.5 hours. |
| 18 | Remove flasks from incubator and return them to the biological safety hood. |
| 19 | Without touching the bottom of culture flask (do not disturb the adherent cells on the bottom), pipette off the RPMI and discard into waste container. |
| 20 | Carefully add 10 mL of 1xPBS down the inner side of each culture flask and rock gently. |
| 21 | Pipette off the PBS containing any undesired non-adherent cells and discard into waste container. |
| 22 | Repeat steps 20 and 21 two more times. |
| 23 | Gently add 15 mL complete DC Media (containing IL-4, GM-CSF, and Gentamycin) to each flask by pipetting down the inner side of it. |
| 24 | Write "Culture Day 1" on the flasks, and place in the 37° $CO_2$ incubator for 22-24 hours. |
| 25 | On Day 2, continue with inoculation of cultures with YWCP's and cytokines. |

Example 16: Generation of Dendritic Cells Combined with Loaded YCWP's

Following the procedures in Example 15, the following methods are performed:

I. Addition of YCWP

| STEP | PROCEDURE/WORK INSTRUCTIONS |
|---|---|
| 1 | To each dendritic cell culture flask, add a sufficient volume of loaded YCWP at a ratio of 1:100. (50-200 ul) and incubate for 1-2 hours. |

II. Preparation And Addition of Cytokines

| STEP | PROCEDURE/WORK INSTRUCTIONS |
|---|---|
| 1 | Add TNF-α, 1β, IL-6 and PGE2 to each culture flask, |

Example 17: Harvest of Cells, Preparation and Cryopreservation of Vaccine Composition The following methods are performed:
Harvest of cells:

| STEP | PROCEDURE/WORK INSTRUCTIONS |
|---|---|
| 1 | Add 4.0-4.5 mL 1xPBS to each flask containing 10 mL media. |
| 2 | Add 1.5-2.0 mL CellStripper ™ to each flask to release mature cells and incubate at 37° C. |
| 3 | Centrifuge and remove supernatant by decanting until "dry" pellet remains. |

II. Preparation of Vaccine Composition and Cryopreservation:

| STEP | PROCEDURE/WORK INSTRUCTIONS |
|---|---|
| 1 | Resuspend cells in CryoStor ™ 10, aliquot and step down freeze. |

Example 18: Experiment in Mouse Model

B16 murine tumor lysate loaded yeast cell wall particles was used as a vaccine for mice. Mice not vaccinated and inoculated with one million B16 tumor cells IV were used as control. Three days prior to tumor challenge with the same tumor load IV, mice were vaccinated: (i) with tumor lysate and yeast cell wall particles simply mixed; or (ii) with yeast cell wall particles loaded with the tumor lysate. The total protein content of tumor lysate and the number of yeast cell walls for both groups of the vaccinated mice were identical. 21 days following inoculation with one million B16 tumor cells IV, the lungs of the mice of each group were examined.

Figure 6A:
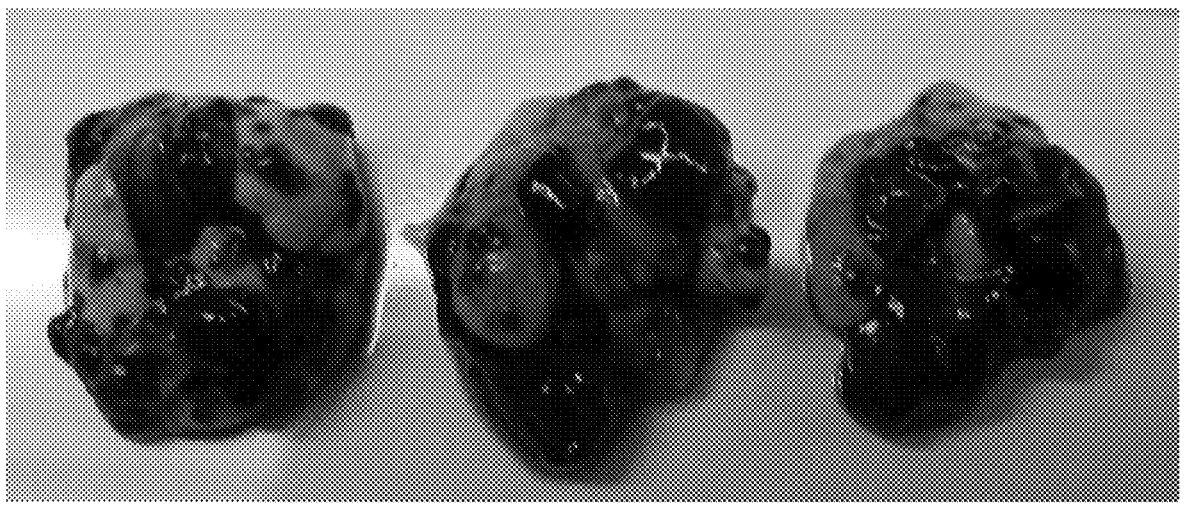
FIG. 6A depicts the lungs of unvaccinated mice 21 days following inoculation with one million B16 tumor cells IV (dark spots are melanoma metastases).
Figure 6B:
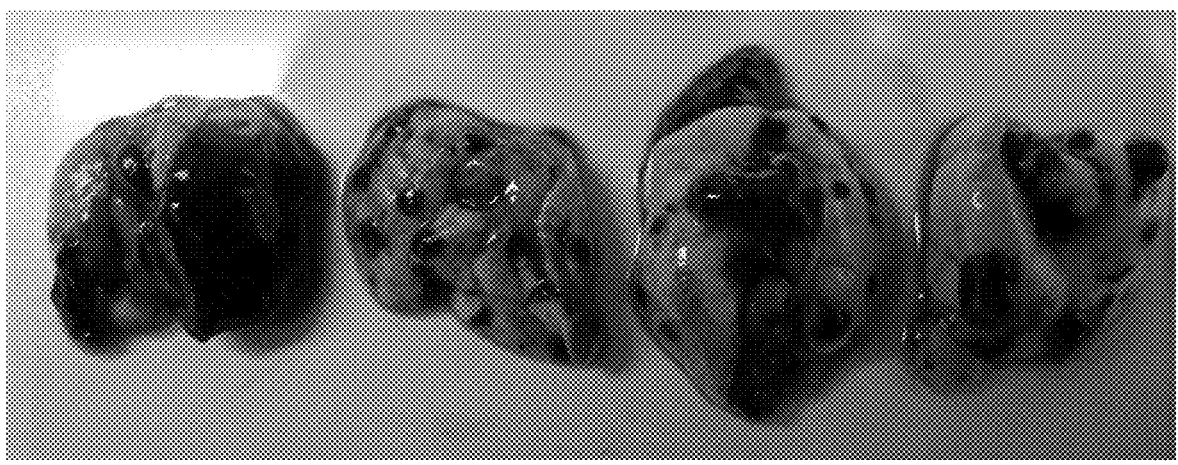
FIG. 6B depicts the lungs of vaccinated mice 21 days following inoculation with one million B16 tumor cells IV, which mice were vaccinated with tumor lysate and yeast cell wall particles simply mixed 3 days prior to tumor challenge.
Figure 6C:
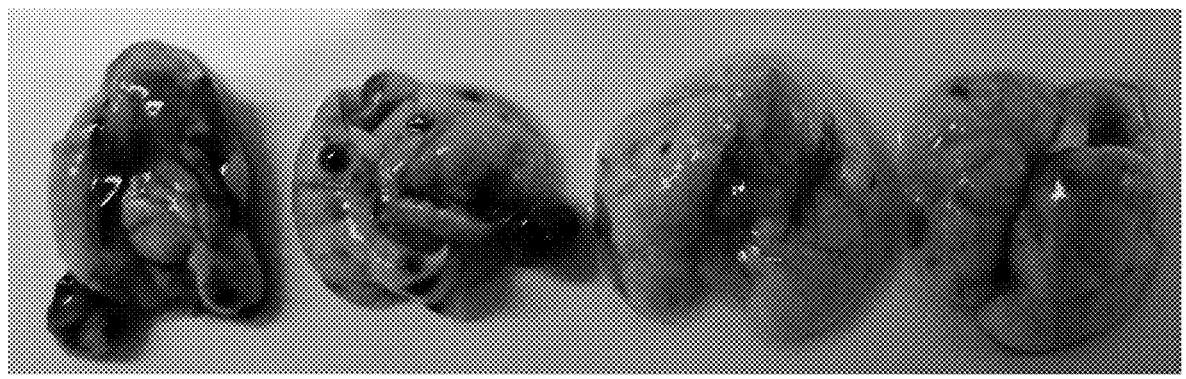
FIG. 6C depicts the lungs of vaccinated mice 21 days following inoculation with one million B16 tumor cells IV, which mice were vaccinated with yeast cell wall particles loaded with tumor lysate 3 days prior to tumor challenge.

FIGS. 6A, 6B and 6C show the results of the lungs of the mice of each group 21 days following tumor challenge.

Example 19: Preparing Silicate Capped Yeast Cell Wall Particles

Yeast cell wall particles (YCWPs) were prepared and loaded with a peptide as described in the examples above. 1 mg of YCWPs were loaded with 500 μg of the peptide. Subsequently, the freeze dried, loaded YCWPs were suspended in 1 ml of absolute ethanol, to which suspension 100 μl of tetraethylorthosilicate and 100 μl of a 10% aqueous ammonia solution were added. The mixture was shaken gently for 15 minutes at room temperature. The YCWPs were then washed thoroughly with absolute ethanol and kept in ethanol at 4° C. until use.

Example 20: In Vitro Leaking Assay

The YCWPs were loaded with fluorescence labeled albumin and then a portion of the loaded YCWPs were capped with silicate according to the example above while others remain uncapped.

Both the uncapped and silicate capped YCWPs loaded with fluorescence labeled albumin were first read on a reader to obtain the initial reading to the total fluorescence counts, and then both the uncapped and silicate capped YCWPs were shaken vigorously. Supernatants were taken from both the uncapped and the silicate capped YCWPs at one hour and at two hours to obtain the fluorescence readings, detailed below.

|  | PBS (control) | Uncapped YCWPs | Silicate Capped YCWPs |
|---|---|---|---|
| Initial fluorescence counts | 8879 | 59645 | 175861 |
| Fluorescence counts of supernatants after 1-hour shaking | 6329 | 14751 | 27797 |
| Fluorescence counts of supernatants after 1-hour shaking | 5944 | 9893 | 11700 |

As shown in the table above, after one hour of shaking, uncapped YCWPs leaked 24.73% of the total fluorescence and silicate capped YCWPs leaked 15.81% of the total fluorescence. After two hours of shaking, uncapped YCWPs leaked 16.6% of the total fluorescence and silicate capped YCWPs leaked 6.65% of the total fluorescence. In summary after two hours, the uncapped YCWPs lost 41.33% of the fluorescent labeled albumin while the silicate capped YCWPs lost only 22.46% of the loaded albumin.

Example 21: In Vivo Loading Release Assay

Mouse macrophage Raw cells, a phagocytic monocytic cell line, were plated in 6-well plate and cultured overnight. Uncapped YCWPs and silicate capped YCWPs, both loaded with fluorescence labeled albumin, were added into the cells on the second day morning. After overnight culture, cells were washed several times with PBS and lysed. Lysates were centrifuged to collect supernatants to obtain fluorescence readings. The supernatant and pellet of the uncapped YCWPs had fluorescence counts of 1042 and 1094 respectively; whereas the supernatant and pellet of the silicate capped YCWPs had fluorescence counts of 1945 and 878 respectively. As such, the silicate capped YCWPs delivered 86.6% more released albumin into the cytoplasm of the phagocytic cells than the uncapped YCWPs did.

Example 22: In Vitro Phagocytosis Assay

Mouse macrophage Raw cells were plated in 24-well plate and cultured overnight. Uncapped YCWPs and silicate capped YCWPs, both loaded with fluorescence labeled albumin were added into the cells on the second day morning. Cell fluorescence readings were measured at 20 minutes, 1 hour, and 2 hours, respectively.

| Fluorescence Counts | | 20 minutes | 1 hour | 2 hours |
|---|---|---|---|---|
| Uncapped YCWPs | 10 μl | 3560 | 3123 | 3193 |
|  | 30 μl | 3485 | 3137 | 3571 |
|  | 60 μl | 3579 | 3442 | 3928 |
| Silicate capped YCWPs | 10 μl | 3499 | 3754 | 4624 |
|  | 30 μl | 3408 | 4599 | 6213 |
|  | 60 μl | 4408 | 6944 | 11065 |

As shown in the table above, the silicate capped YCWPs delivered 82% more loaded albumin into the phagocytic cells than the uncapped YCWPs did.

Example 23: Mouse Survival Study

Survival study was performed on five groups of mice, with 5 mice in each group of Groups I-IV and 10 mice in Group V. The control group (Group I) received $0.5 \times 10^6$ B16 melanoma tumor cells by IV injection. The "regular YCWP" group (Group II) received $0.5 \times 10^6$ B16 melanoma tumor cells by IV injection and vaccination by interdermal injection one week prior to and each week following tumor cell IV injection with uncapped YCWPs loaded with B16 tumor lysate until week 6. The "Si capped YCWPs" group (Group III) received $0.5 \times 10^6$ B16 melanoma tumor cells by IV injection and vaccination by interdermal injection one week prior to and each week following tumor cell IV injection with silicate capped YCWPs loaded with B16 tumor lysate until week 6. The "regular YCWPs+AD" group (Group IV) received $0.5 \times 10^6$ B16 melanoma tumor cells by IV injection and vaccination by interdermal injection one week prior to and each week following tumor cell IV injection with uncapped YCWPs loaded with B16 tumor lysate, and GpC Oligonucleotide and Monophosphoryl lipid A adjuvants until week 6. The "Si capped YCWP+AD group" (Group V) received $0.5 \times 10^6$ B16 melanoma tumor cells by IV injection and vaccination by interdermal injection one week prior to and each week following tumor cell IV injection with silicate capped YCWPs loaded with B16 tumor lysate, and GpC oligonucleotide and monophosphoryl lipid A adjuvants until week 6.

Figure 8:
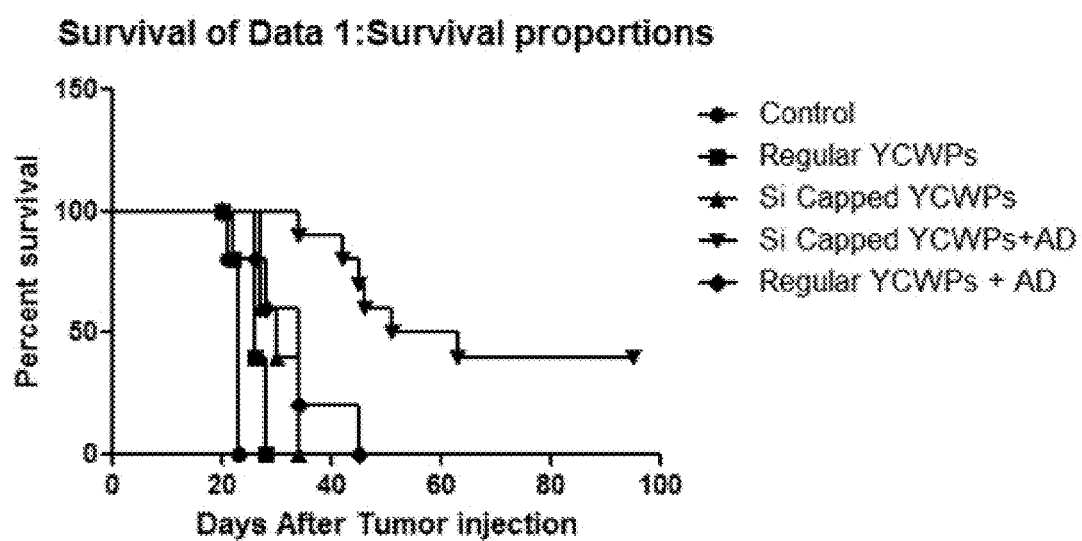
FIG. 8 depicts the percentage of survival of each group of the mice: "control" group that received IV injection of B16 melanoma tumor cells only; "regular YCWP" group that received IV injection of B16 melanoma tumor cells and interdermal injection of uncapped YCWPs loaded with B16 tumor lysate; "Si capped YCWP" group that received IV injection of B16 melanoma tumor cells and interdermal injection of silicate capped YCWPs loaded with B16 tumor lysate; "regular YCWPs+AD" group that received IV injection of B16 melanoma tumor cells and interdermal injection of uncapped YCWPs loaded with B16 tumor lysate and adjuvants including CpG oligonucleotide and monophosphoryl lipid A, and "Si capped YCWPs+AD" group that received IV injection of B16 melanoma tumor cells and interdermal injection of silicate capped YCWPs loaded with B16 tumor lysate and adjuvants including CpG oligonucleotide and monophosphoryl lipid A.

As shown in FIG. 8, all mice in the control group died in about 22 days. All mice in the regular YCWP group died in about 25 days, all mice in the silicate capped YCWP group died in about 35 days, and all mice in the regular YCWP and adjuvant group dies in about 45 days. In contrast, about 40% of the mice in the silicate capped YCWP and adjuvant group survived after 100 days.

What is claimed is:

1. A vaccine comprising (i) a yeast cell wall particle (YCWP), (ii) a viral antigen or bacterial antigen loaded into the yeast cell wall particle, and (ii) a silicate, wherein the YCWP is modified by capping with the silicate, wherein the viral antigen or bacterial antigen is not a tumor lysate, wherein the yeast cell wall particle is a hollow, porous structure, and wherein the vaccine does not comprise a cell of monocytic origin.

2. The vaccine of claim 1, wherein the silicate is tetraethylorthosilicate, tetramethylorthosilicate, tetrapropylorthosilicate, or tetrabutylorthosilicate.

3. The vaccine of claim 1, wherein the silicate comprises an organic moiety attached to each of the four oxygen compounds of an orthosilicate.

4. A method of treating an infectious disease, comprising administering to a subject the vaccine of claim 1.

5. A method for producing a yeast cell wall particle loaded with a biological material and capped with a silicate, comprising:
   (i) loading a biological material into a yeast cell wall particle to produce a loaded particle wherein the biological material comprises a protein or a fragment thereof, nucleic acid, carbohydrate, antigen or a combination thereof, and wherein the biological material is viral antigen, or bacterial antigen;
   (ii) capping the loaded particle with a silicate; and
   (iii) freeze-drying the capped, loaded particle.

* * * * *